United States Patent
Stametz et al.

(10) Patent No.: US 8,214,996 B2
(45) Date of Patent: Jul. 10, 2012

(54) SURGICAL NEEDLE SWAGE TOOL

(75) Inventors: Jerry Stametz, Cornelia, GA (US); John Price, Seneca, SC (US); Eugene Reynolds, Avon by the Sea, NJ (US); Kenneth Barsch, San Angelo, TX (US)

(73) Assignee: Ethicon, Inc., Somerville, NJ (US)

( * ) Notice: Subject to any disclaimer, the term of this patent is extended or adjusted under 35 U.S.C. 154(b) by 778 days.

(21) Appl. No.: 12/330,702

(22) Filed: Dec. 9, 2008

(65) Prior Publication Data

US 2010/0139883 A1  Jun. 10, 2010

(51) Int. Cl.
*B21D 39/00* (2006.01)
*B21G 1/12* (2006.01)

(52) U.S. Cl. ............................................. 29/515; 163/5

(58) Field of Classification Search .................. 29/515, 29/505, 428, 465, 407.08, 517, 518; 165/5, 165/1; 163/5, 1
See application file for complete search history.

(56) References Cited

U.S. PATENT DOCUMENTS

| | | |
|---|---|---|
| 1,558,037 A | 10/1925 | Morton |
| 1,665,216 A | 4/1928 | Morton |
| 2,008,227 A | 7/1935 | Reilly |
| 2,131,766 A | 10/1938 | Temple |
| 2,621,385 A | 12/1952 | Gilmore |
| 2,741,752 A | 4/1956 | Edwards |
| 2,802,468 A | 8/1957 | Everett et al. |
| 2,910,983 A | 11/1959 | Everett |
| 2,928,395 A | 3/1960 | Forbes et al. |
| 3,394,704 A | 7/1968 | Dery |
| 3,799,169 A | 3/1974 | Beroff et al. |
| 3,890,975 A | 6/1975 | McGregor |
| 3,910,282 A | 10/1975 | Messer et al. |
| 3,924,630 A | 12/1975 | Walldorf |
| 4,054,144 A | 10/1977 | Hoffman et al. |
| 4,060,885 A | 12/1977 | Hoffman et al. |
| 4,072,041 A | 2/1978 | Hoffman et al. |
| 4,124,027 A | 11/1978 | Boss |
| 4,127,133 A | 11/1978 | Martinez |
| 4,182,341 A | 1/1980 | Perri |
| 4,630,617 A | 12/1986 | Ritter et al. |

(Continued)

FOREIGN PATENT DOCUMENTS

AU  B-58368/80  8/1980

(Continued)

OTHER PUBLICATIONS

International Patent Application No. PCT/US2009/066772, filed Apr. 12, 2009, entitled: "Surgical Needle Swage Tool".

(Continued)

*Primary Examiner* — John C Hong
(74) *Attorney, Agent, or Firm* — Greenberg Traurig (57) ABSTRACT

In a method of attaching a suture to a needle barrel, a first compression stroke compresses the radially-defined top of the barrel against a suture in the bore of the barrel while restraining the bottom and sides of the barrel against deformation. A second compression stroke compresses the bottom of the barrel against the suture while restraining the sides against deformation. In another method, the top and bottom are compressed concurrently while the sides are restrained against deformation. An apparatus for attaching a suture to a needle barrel includes two die sets, each including a die with a groove therein. In one die set, the groove protects the bottom and sides of the barrel from deformation while the top is compressed. In the other die set, the groove protects the sides of the barrel from deformation while the bottom is compressed.

16 Claims, 10 Drawing Sheets

U.S. PATENT DOCUMENTS

| | | | |
|---|---|---|---|
| 4,799,484 A | 1/1989 | Smith et al. |
| 4,832,025 A | 5/1989 | Coates |
| 4,922,904 A | 5/1990 | Uetake et al. |
| 5,000,912 A | 3/1991 | Bendel et al. |
| 5,007,922 A | 4/1991 | Chen et al. |
| 5,046,350 A | 9/1991 | Proto et al. |
| 5,099,676 A | 3/1992 | Proto et al. |
| 5,131,131 A | 7/1992 | Proto et al. |
| 5,139,514 A | 8/1992 | Korthoff et al. |
| 5,156,615 A | 10/1992 | Korthoff et al. |
| 5,168,619 A | 12/1992 | Proto et al. |
| 5,201,760 A | 4/1993 | West |
| 5,207,701 A | 5/1993 | West |
| 5,224,955 A | 7/1993 | West |
| 5,259,846 A | 11/1993 | Granger et al. |
| 5,268,014 A | 12/1993 | Miller et al. |
| 5,350,373 A | 9/1994 | Colligan |
| 5,383,902 A | 1/1995 | Carpentiere et al. |
| 5,394,726 A | 3/1995 | Bogart et al. |
| 5,403,345 A | 4/1995 | Spingler |
| 5,438,746 A | 8/1995 | Demarest et al. |
| 5,462,543 A | 10/1995 | Colligan |
| 5,473,810 A | 12/1995 | Demarest et al. |
| 5,487,212 A | 1/1996 | Demarest et al. |
| 5,487,216 A | 1/1996 | Demarest et al. |
| 5,487,308 A | 1/1996 | Demarest et al. |
| 5,495,420 A | 2/1996 | Demarest et al. |
| 5,500,991 A | 3/1996 | Demarest et al. |
| 5,507,798 A | 4/1996 | Colligan et al. |
| 5,568,746 A | 10/1996 | Colligan et al. |
| 5,569,302 A | 10/1996 | Proto et al. |
| 5,593,425 A | 1/1997 | Bonutti et al. |
| 5,608,962 A | 3/1997 | Colligan et al. |
| 5,651,843 A | 7/1997 | Bendel et al. |
| 5,697,134 A | 12/1997 | Spaulding et al. |
| 5,707,391 A | 1/1998 | Carpentieri |
| 5,713,116 A | 2/1998 | Nickerson et al. |
| 5,722,991 A | 3/1998 | Colligan |
| 5,844,142 A | 12/1998 | Blanch et al. |
| 5,891,164 A | 4/1999 | Dabir et al. |
| 6,012,216 A | 1/2000 | Esteves et al. |
| 6,031,018 A | 2/2000 | Scopelianos et al. |
| 6,032,343 A | 3/2000 | Blanch et al. |
| 6,056,771 A | 5/2000 | Proto |
| 6,081,981 A | 7/2000 | Demarest et al. |
| 6,163,948 A | 12/2000 | Esteves et al. |
| 6,263,558 B1 | 7/2001 | Blanch et al. |
| 6,322,582 B1 | 11/2001 | Richard et al. |
| 6,360,415 B1 | 3/2002 | Wada et al. |
| 6,877,352 B1 | 4/2005 | Schlereth |
| 6,939,365 B1 | 9/2005 | Fogarty et al. |
| 7,165,311 B2 | 1/2007 | Schwar |
| 7,322,086 B2 | 1/2008 | Humpert et al. |
| 7,591,054 B2 | 9/2009 | Baughman |
| 2005/0113869 A1 | 5/2005 | Price |
| 2008/0119876 A1 | 5/2008 | Price et al. |
| 2008/0161850 A1 | 7/2008 | Weisenburgh et al. |

FOREIGN PATENT DOCUMENTS

| | | |
|---|---|---|
| JP | 405154158 A1 | 6/1993 |
| JP | 2002034992 A | 2/2002 |

OTHER PUBLICATIONS

International Search Report and Written Opinion for PCT/US2009/066772, mailed Feb. 19, 2010.

Technical Data Sheet Product 4302, Locite Corporation, Rocky Hill, CT, May 1998, pp. 1-2.

SURGICAL NEEDLE SWAGE TOOL

FIELD OF INVENTION

The present invention relates to apparatus and methods for attaching needles to sutures, such as for making armed sutures for surgical applications, and, more particularly, to apparatus and methods for attaching surgical needles to sutures using a swaging process.

BACKGROUND OF INVENTION

Various methods for swaging needles to sutures are known. In a surgical needle of a well-known type, the free end of a suture is inserted into an axial bore within a blunt end of the needle (the "needle barrel"), and held in that position while a swage die impinges upon the outer surface of the needle barrel, thereby compressing a portion of the bore onto the suture. The compressed portion of the bore grasps the suture by mechanical interference and by surface contact (friction). The swaging process is conducted so as to create an attachment between the needle barrel and suture that meets or exceeds the attachment (or "pull-out") strength requirements of standards such as USP 23 <871>.

One approach to providing good suture attachment is multiple hit swaging, wherein a needle is subjected to swaging (i.e., compression) of controlled depth, but distributed over a large area (e.g., around the circumference of the needle). To achieve this type of swaging, the needle may be rotated relative to the swaging dies between multiple swaging compressions. In this manner, multiple angularly offset swaging operations (hits) are performed to attach a single needle to a single suture. While this approach provides good attachment, each hit on the barrel of the needle produces stress in the needle barrel and suture. The materials of which the needle and suture are made inherently have some degree of malleability, but when the limit of malleability is reached, the material will fail, leading to, in the case of the needle, cracking and loss of attachment, or breakage. Cracking is a particular problem when harder alloys are used, including advanced alloys such as 4310 SS, nickel-titanium SS, and 420 SS. Further, needle materials have some elasticity, such that the relief of residual stress causes the needle barrel to relax over time, leading to a loss of attachment between the needle bore and the suture.

SUMMARY OF THE INVENTION

In one embodiment, the invention relates to an apparatus for attaching a suture to a needle barrel. The needle barrel has a first radially-defined portion (or "top"), and a second radially-defined portion (or "bottom") opposite the first radially-defined portion, first and second lateral portions (or "sides") between the top and bottom and opposite each other, and a bore formed in an end of the needle barrel for receiving an end of the suture. The apparatus includes a first die set including first and second dies, at least one of which is movable relative to the other. The first die has a groove therein for receiving the needle barrel such that moving one or both of the first and second dies toward the other causes the second die to compress the top of the needle barrel so as to compress the suture against the inner surfaces of the bore. The groove of the first die is at least partially defined by a curved surface sized and shaped so as to protect the bottom and sides of the needle barrel from becoming substantially deformed during the compression of the top of the needle barrel. The apparatus further includes a second die set including third and fourth dies, at least one of which is movable relative to the other. The third die has a groove therein for receiving the needle barrel such that moving one or both of the third and fourth dies toward the other causes the fourth die to compress the bottom of the needle barrel so as to compress the suture against the inner surfaces of the bore. The groove of the third die is at least partially defined by a curved surface sized and shaped so as to protect the sides of the needle barrel from becoming substantially deformed during the compression of the bottom of the needle barrel.

Another embodiment of the invention relates to a method of attaching a suture to the aforementioned type of needle barrel using two compression strokes. The first compression stroke compresses the top of the needle barrel such that the suture is compressed against the inner surfaces of the bore while the bottom and sides of the needle barrel are restrained so as to protect them from becoming substantially deformed. The second compression stroke is performed so as to compress the bottom of the needle barrel such that the suture is further compressed against the inner surfaces of the bore while the sides of the needle barrel are restrained so as to protect them from becoming substantially deformed.

Yet another embodiment of the invention relates to a method of attaching a suture to the aforementioned type of needle barrel using one compression stroke. The top and bottom of the needle barrel are compressed concurrently with a flat surface of a first tool and a flat surface of a second tool, respectively, such that the suture is compressed against the inner surfaces of the bore while the sides of the needle barrel are restrained so as to protect them from becoming substantially deformed.

A further embodiment of the invention relates to a combination of a suture and a needle having a needle barrel. The needle barrel has a cross-sectional shape having opposed outwardly curved portions and opposed substantially flat portions between the curved portions, and is substantially symmetrical about a first plane passing through a central longitudinal center axis of the needle barrel and substantially perpendicularly through the flat portions of the cross-section. An end of the suture is compressed against the inner surfaces of the bore.

DETAILED DESCRIPTION OF THE INVENTION

Figure 1:
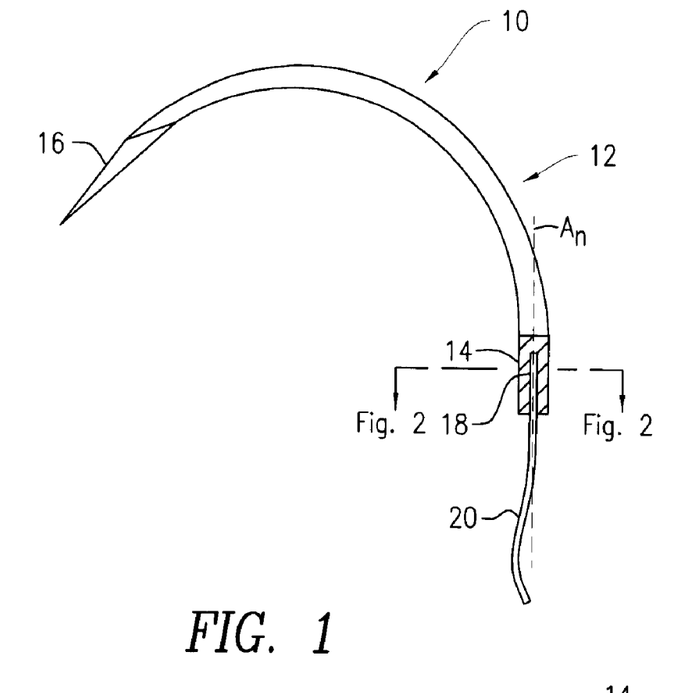
FIG. 1 is a partially-cutaway view of a surgical needle of a type for use with a swage die set according to the present invention.
Figure 2:
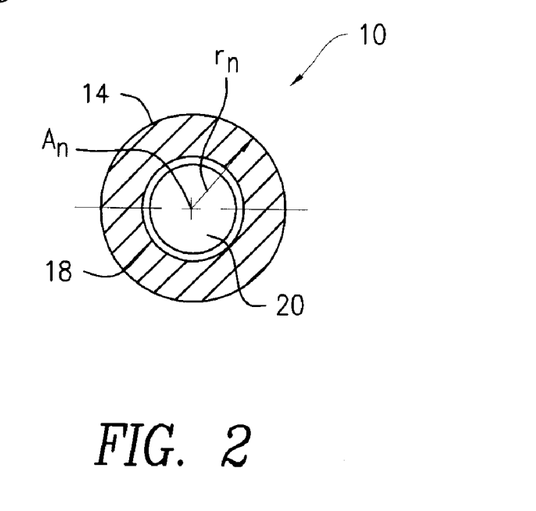
FIG. 2 is a cross-sectional end view of the needle barrel of the surgical needle of FIG. 1.

The devices and methods described herein are intended for use with a surgical needle (subsequently, "the needle"), such as the unswaged needle 10 depicted in FIGS. 1 and 2. The needle 10 may have a curved body 12 having a tubular end 14 (subsequently, "the needle barrel") and a sharp end 16. The needle barrel 14 includes a straight bore 18 that opens outwardly (shown in FIG. 1 in a cutaway view) opposite the sharp end 16. FIG. 2 is a cross-sectional end view of the needle barrel 14, which will typically have a circular cross-section with a radius $r_n$ about a central longitudinal axis $A_n$. The needle barrel 14 can be provided with a radius $r_n$ in the range of radiuses of conventional wire sizes (e.g., about 0.003 inches to about 0.035 inches). The needle 10 may be made of any one of a number of metal alloys, including, but not limited to, 4310 SS, nickel-titanium (NiTi) SS and 420 SS, or advanced alloys, such as, tungsten-rhenium (W—Re) alloys and refractory alloys. The bore 18 is sized and shaped to receive a suture 20, which may be one of any number of well-known types, or of types yet to be developed.

FIGS. 3-18 illustrate a process and apparatus in accordance with a first embodiment of the present invention for swaging the needle barrel 14 to the suture 20 in which the needle barrel 14 is compressed against the suture 20 in two separate, sequential compression strokes (i.e., a "two-hit" process). The first stroke is performed using a first set of dies at a first work station while the second stroke is performed using a second set of dies at a second work station. In accordance with an alternate embodiment of the invention, both strokes may be performed at a single work station using a single set of dies, as described separately below.

First and second die sets for use in the two-hit process are illustrated in FIGS. 3-6 and 7-10, respectively, in which the die sets, and the sections thereof, are shown oriented in a vertical direction. However, the first or second die sets could be oriented horizontally or in any other direction, as long as the respective dies in each set are substantially opposed to each other and their respective movement is approximately along the same axis, such that they converge and diverge. Terms indicating position, orientation and direction of motion are used throughout the discussion of FIGS. 2-18 in relation to the first and second die sets as illustrated in FIGS. 2-10 for the purpose of facilitating discussion, and not to limit the embodiments to the particular ones shown and described.

Figure 3:
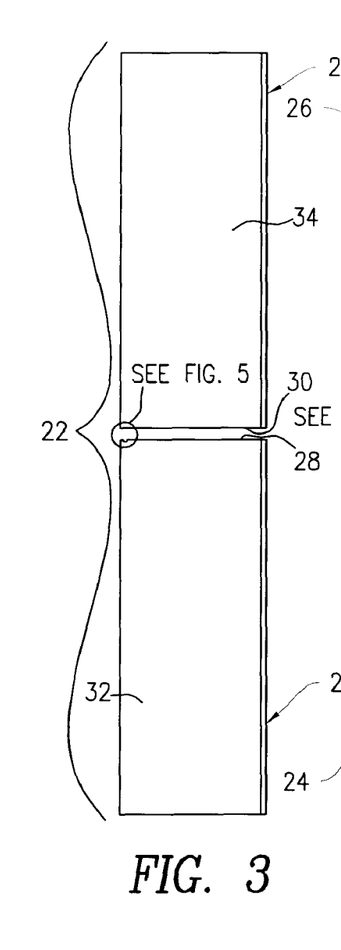
FIG. 3 is a front view of a first swage die set according to a first embodiment of present invention for making a first compression stroke of a two-hit swage process.
Figures 4, 5, 6:
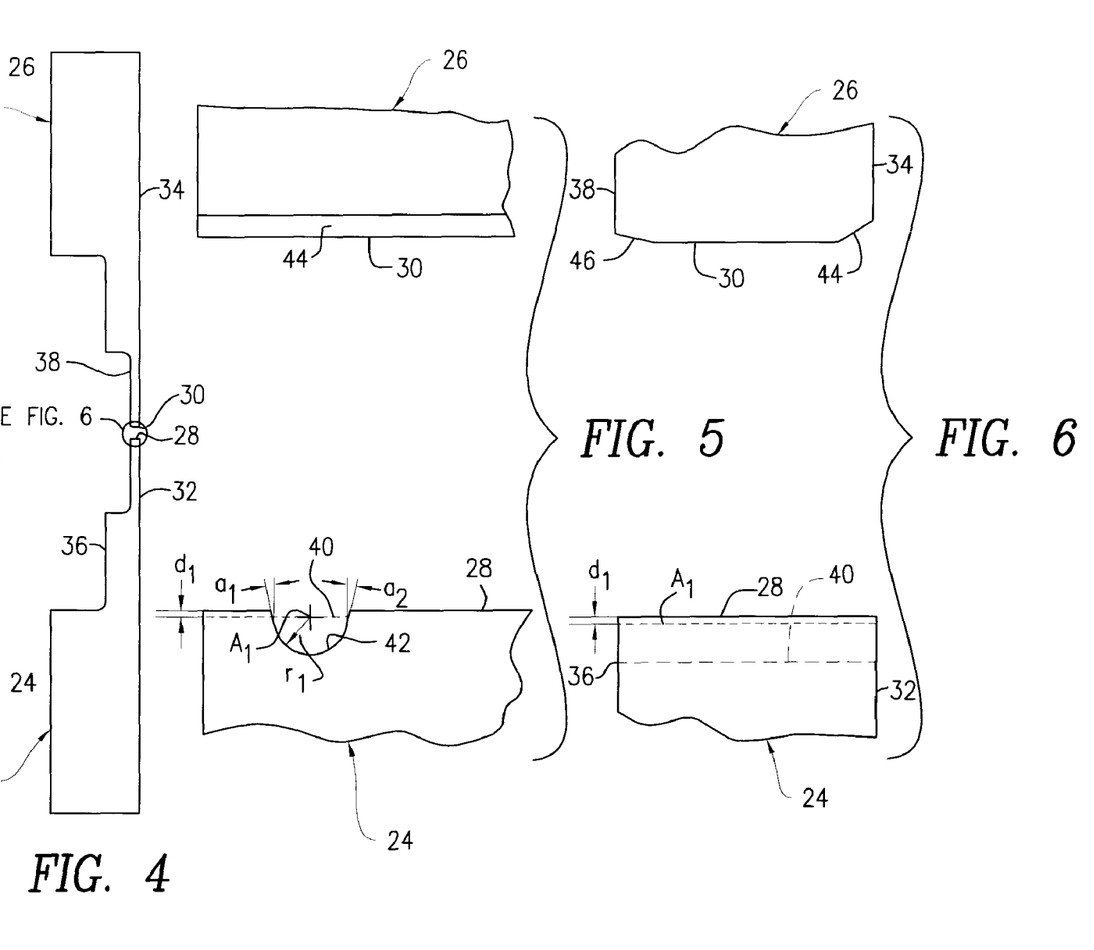
FIG. 4 is a side view of the swage die set of FIG. 3.
FIG. 5 is an enlarged view of a portion of the swage die set of FIG. 3.
FIG. 6 is an enlarged view of a portion of the swage die set shown in FIG. 4.

Turning to FIGS. 3 and 4, the first die set 22 includes a lower die 24 and an upper die 26 that is opposable to the lower die 24. In an embodiment of the invention, the dies 24, 26 are adapted to be mounted on conventional needle-swaging machinery (not shown) at a first swaging station. The lower and upper dies 24, 26 are shown as having substantially the same relative positions and orientations that they would have at the start of the two-hit process, with an upper surface 28 of the lower die 24 opposed to and separated from a lower surface 30 of the upper die 26. The aforesaid upper surface 28 and lower surface 30 are adapted to closely approach one another during the swaging process. For reference, the dies 24, 26 also have respective front surfaces 32, 34 and respective back surfaces 36, 38. Each of the front surfaces 32, 34 and back surfaces 36, 38 is also referred to herein as a needle side 32, 34 or suture side 36, 38, respectively, because, during the swaging process, the portion of the needle that is not compressed will extend away from the front surface 32, 34 and the suture 20 will extend away from the back surface 36, 38.

FIGS. 5 and 6 are enlarged views of the sections of the lower and upper dies 24, 26 that are indicated in FIGS. 3 and 4, respectively. As shown in FIG. 5, the lower die 24 has a groove 40 with a cylindrically-curved surface 42 having a substantially constant radius r, about a longitudinal axis $A_1$ over an arc of about 180 degrees or less. The axis $A_1$ of the curved surface 42 is set back from the upper surface 28 of the lower die 24 by a distance $d_1$. In one embodiment of the invention, the curved surface 42 is flared outward by angles $a_1$ and $a_2$ adjacent the upper surface 28 to facilitate placement and removal of the needle barrel 14. In one embodiment of the invention, angles $a_1$ and $a_2$ are about 8 degrees, individually. In other embodiments, angles $a_1$ and $a_2$ may be as small as 0 degrees. The radius $r_1$ of the curved surface 42 and the set-back distance $d_1$ are selected so that the needle barrel 14 to be swaged would be restrained laterally at its opposed sides during the first compression stroke when resting against the curved surface 42 such that its axis $A_n$ generally coincides with the axis $A_1$ of the curved surface 42. In one embodiment of the invention, the radius $r_1$ of the curved surface 42 is approximately the same as the radius $r_n$ of the portion of the needle barrel 14 that is to be swaged, and the set-back distance $d_1$ is in the range of about 25 percent to about 40 percent of the radius $r_n$. For example, to accommodate a needle 14 having a radius $r_n$ of about 0.005 inches, the lower die 24 may have a curved surface 42 with a radius $r_1$ of about 0.005 inches, and a set-back distance $d_1$ of about 0.002 inches. The remainder of the upper surface 28 of the lower die 24 is substantially flat. It can be seen that the lower surface 30 of the upper die 26 is also substantially flat.

As shown in FIG. 6, the upper surface 28 of the lower die 24 is substantially flat from the front surface 32 of the lower die 24 to its back surface 36. In the embodiment shown, the groove 40 extends from the needle side 32 to the suture side 36 of the lower die 24. In an alternate embodiment, the groove 40 may terminate near the suture side 36 with a smaller-diameter groove or aperture provided at the suture side 36 to receive the suture 20. The lower surface 30 of the upper die 26 is chamfered to form chamfers 44, 46 at the needle-side 34 and suture-side 38, respectively. The chamfers 44, 46 are provided so as to control the stresses placed on the needle barrel 14 and suture 20 during the swaging process. In one embodiment of the invention, the angles of the chamfers 44, 46 relative to the lower surface 30 of the upper die 26 are about 15 degrees for the suture side chamfer 46 and about 30 degrees for the needle side chamfer 44. The entire section of the lower surface 30 that is between the chamfers 44, 46 is substantially flat.

Figures 7, 8:
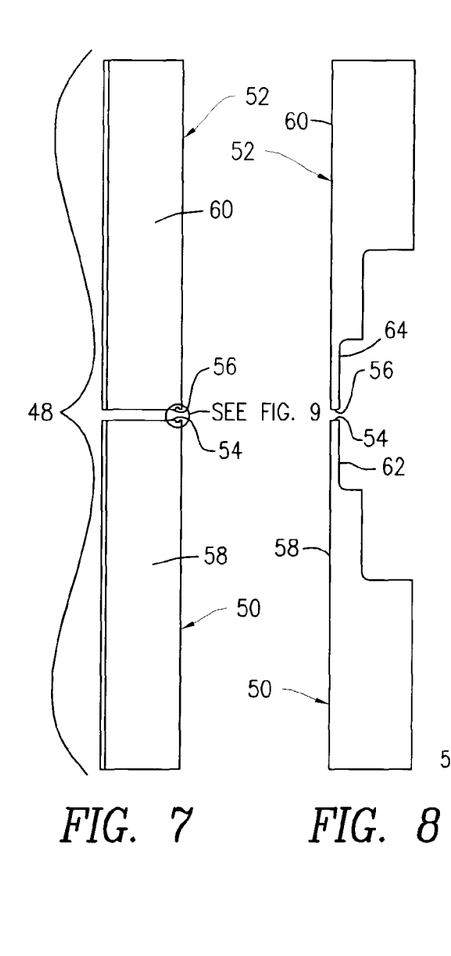
FIG. 7 is a front view of a second swage die set according to the first embodiment of the present invention for making a second compression stroke of the two-hit swage process.
FIG. 8 is a side view of the swage die set of FIG. 7.

Turning to FIGS. 7 and 8, the second die set 48 includes a lower die 50 and an upper die 52 that is opposable to the lower die 50. In an embodiment of the invention, the dies 50, 52 are adapted to be mounted on conventional needle-swaging equipment (not shown) at a second swaging station. The upper and lower dies 50, 52 are shown as having substantially the same relative positions and orientations that they would have at the start of the two-hit process, similar to the arrangement of dies 24 and 26 of FIGS. 3 and 4, with an upper surface 54 of the lower die 50 opposed to and separated from a lower surface 56 of the upper die 52. The aforesaid upper surface 54 and lower surface 52 are adapted to closely approach one another during the swaging process. For reference, the dies 50, 52 also have respective front surfaces 58, 60 (also, "needle sides 58, 60") and respective back surfaces 62, 64 (also, "suture sides 62, 64").

Figures 9, 10:
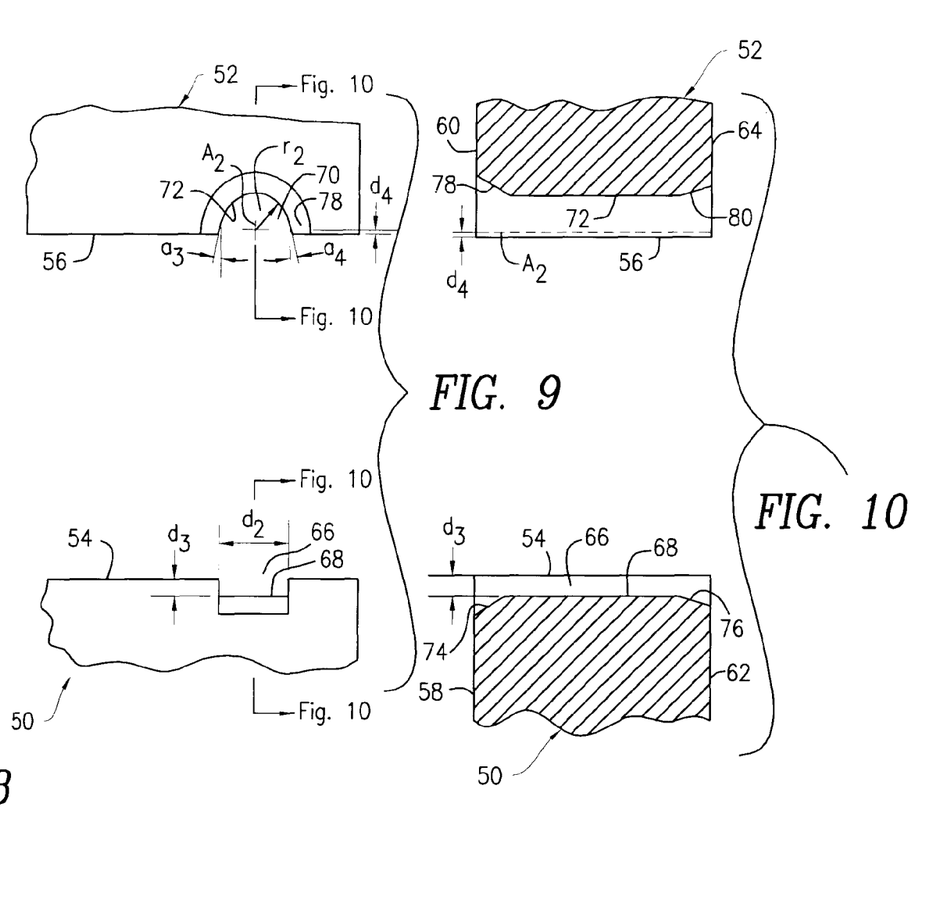
FIG. 9 is an enlarged view of a portion of the swage die set of FIG. 7.
FIG. 10 is cross-sectional side view of the portion of the swage die set of FIG. 9.

FIG. 9 is an enlarged view of the section of the lower die 50, indicated in FIG. 7, while FIG. 10 is a cross-sectional side view of the section shown in FIG. 9. As illustrated FIG. 9, the upper surface 54 of the lower die 50 has a groove 66 having a flat interior surface 68 with a width $d_2$ that is about twice the radius $r_n$ of the needle barrel 14 to be swaged. The flat surface 68 is set back from the upper surface 54 by a set-back distance $d_3$ and is substantially parallel to the upper surface 54. The groove 66 is provided such that the needle barrel 14 would be correctly positioned relative to a groove 70 provided in the die 52 when resting against the flat surface 68. In an embodiment of the invention, this setback distance $d_3$ may be between about 0.002 inches and 0.004 inches. For example, to accommodate a needle barrel 14 having a radius $r_n$ of about 0.005 inches, the set-back distance $d_3$ may be about 0.002 inches, and the width $d_2$ of the groove 66 may be about 0.010 inches.

Continuing with FIG. 9, the groove 70 of the upper die 52 is defined by a cylindrically-curved surface 72 that is sized and shaped to receive the needle barrel 14 with minimal clearance between the needle barrel 14 and the curved surface 72 at least at a set-back distance $d_4$. In the embodiment illustrated in FIG. 9, the curved surface 72 has a substantially constant radius $r_2$ about an axis $A_2$. The radius $r_2$ is approximately the same as, or slightly larger than, the radius $r_1$ of the curved surface 42 of the lower die 24 of the first die set 22 of FIG. 5. The curved surface 72 is flared outward by angles $a_3$ and $a_4$ adjacent the lower surface 56 of the upper die 52 to facilitate entry of the needle barrel 14 into the groove 70, and its subsequent removal. In an embodiment of the invention, the angles $a_3$ and $a_4$ are about 8 degrees, individually. In other embodiments, angles a3 and $a_4$ may be as small as 0 degrees. The axis $A_2$ is set back from the lower edge 56 of the upper die 52 by the set-back distance $d_4$ such that a needle barrel 14 to be swaged would be restrained laterally at its opposed sides during the second compression stroke when its axis $A_n$ generally coincides with the axis $A_2$. For example, to accommodate a needle barrel 14 having a radius of about 0.005 inches before the first compression stroke, the radius $r_2$ may be about 0.0051 inches, and the set-back distance $d_4$ may be about 0.001 inches.

As shown in FIG. 10, the flat surface 68 of the groove 66 of the lower die 50 extends from the needle side 58 to the suture side 62 of the lower die 50 and is chamfered to form chamfers 74, 76, respectively, at the needle side 58 and suture side 62. In an embodiment of the invention, the angles of the chamfers 74, 76 relative to the flat surface 68 is about 30 degrees for the needle-side chamfer 74 and about 15 degrees for the suture-side chamfer 76. The entire section of the flat surface 68 that is between the chamfers 74, 76 is substantially flat.

Continuing to refer to FIG. 10, the curved surface 72 of the upper die 52 is chamfered to form chamfers 78, 80, respectively, at the needle-side 60 and suture-side 64 of the upper die 52. The angles of the needle-side chamfer 78 and the suture-side chamfer 80, relative to the curved surface 72, are selected to be substantially the same as the angles of the needle-side chamfer 44 and the suture-side chamfer 46, respectively, of the upper die 26 of the first die set 22.

FIGS. 11-18 illustrate a two-hit swaging process using the dies 24, 26, 50, 52. FIGS. 11-14 illustrate the first compression stroke of the two-hit swaging process, while FIGS. 15-18 illustrate the second compression stroke. In FIGS. 11-18, cross-hatching has been eliminated from all elements with the exception of the needle barrel 82, to improve the clarity of the drawings, except for the needle barrel 82, described below.

Figure 11:
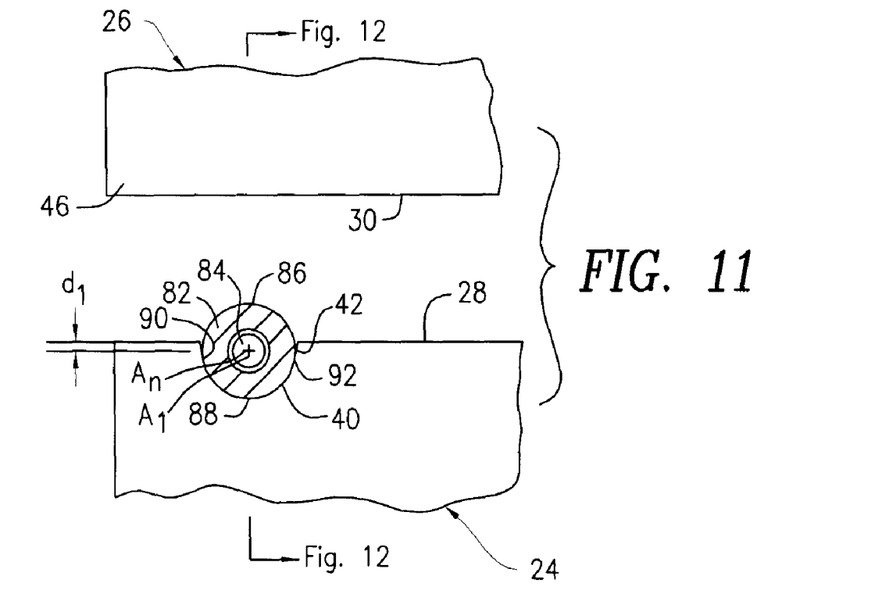
FIG. 11 is a cross-sectional front view of a portion of the swage die set of FIG. 3 with a needle barrel and suture before the first compression stroke of the two-hit swage process.
Figure 12:
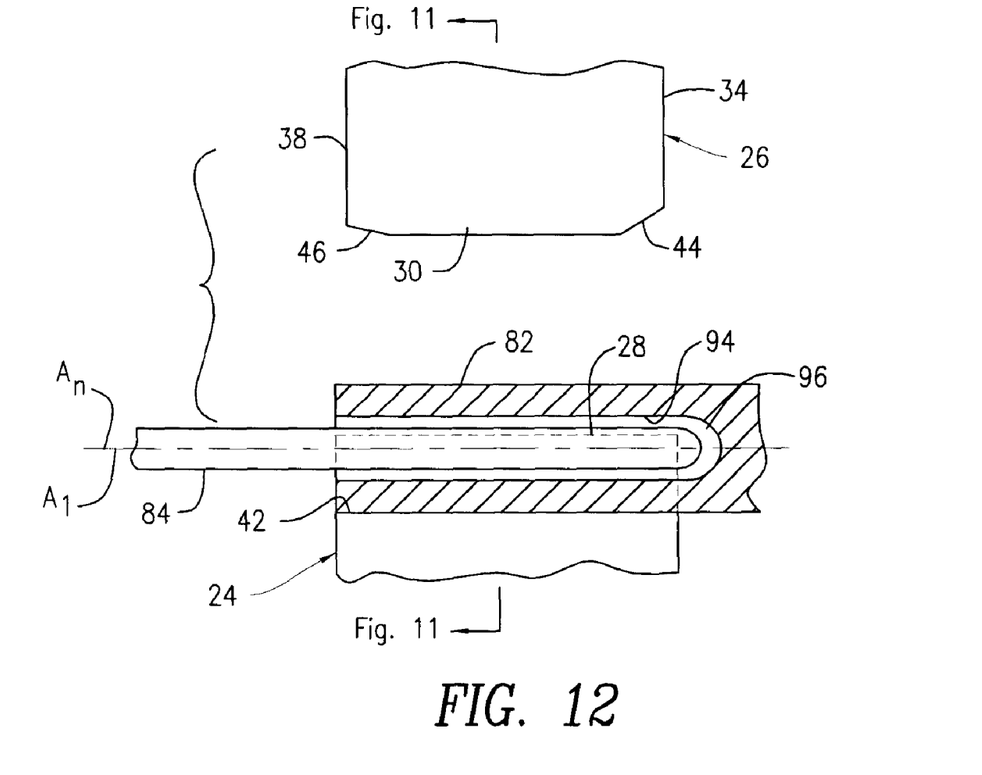
FIG. 12 is a cross-sectional side view of the portion of the swage die set, needle barrel and suture of FIG. 11.

FIGS. 11 and 12 show a cross-sectional front view and cross-sectional side view, respectively, of portions of the dies 24, 26 of the first die set 22 with a needle barrel 82 resting against the curved surface 42 of the groove 40 in the lower die 24, and the upper die 26 positioned above the needle barrel 82. The needle barrel 82 and the suture 84 are of the same types as the needle barrel 14 and the suture 20. For reference, the needle barrel 82 is shown as having a first radially-defined portion 86 (or "top") at a "12 o'clock" position, a second radially-defined portion 88 (or "bottom") at a "6 o'clock" position and opposed first and second lateral portions 90,92 (or "sides") at the "9 o'clock" and "3 o'clock" positions, respectively. It can be seen that the central longitudinal axis $A_n$ of the needle barrel 82 substantially coincides with the axis $A_1$ of the curved surface 42 below the upper surface 28 of the lower die 24. The suture 84 is positioned within the bore 96 of the needle barrel 82, which is at least partially defined by its inner surface 94.

Figure 13:
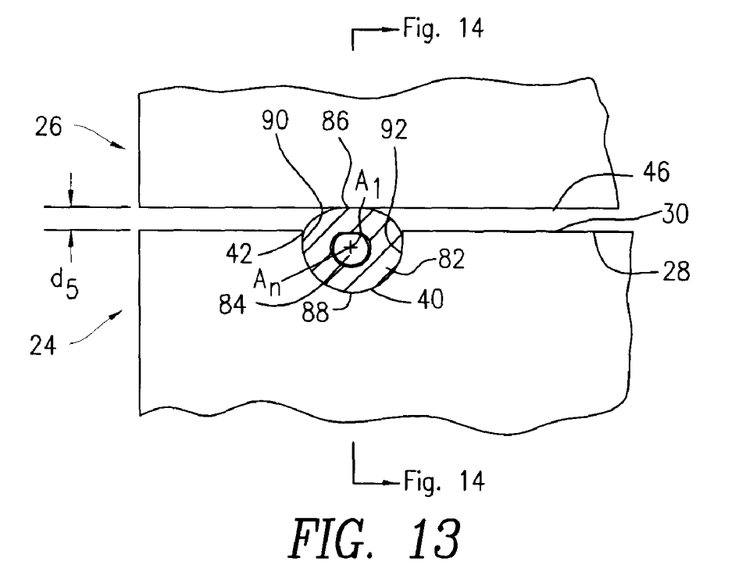
FIG. 13 is a cross-sectional front view of the portion of the swage die set, needle barrel and suture shown in FIG. 11 during the first compression stroke of the two-hit swage process.
Figure 14:
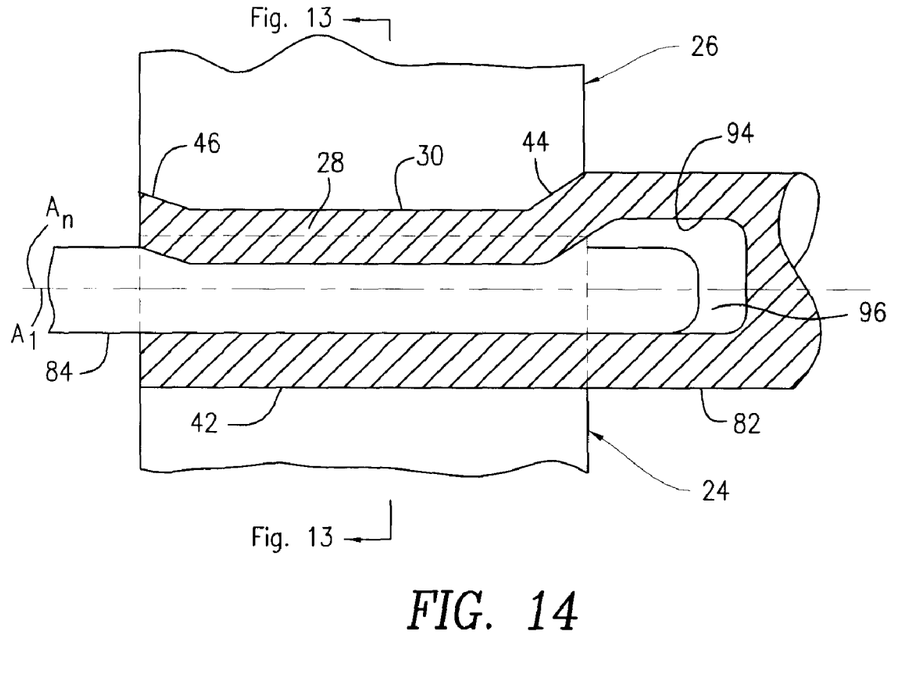
FIG. 14 is a cross-sectional side view of the portion of the swage die set, needle barrel and suture of FIG. 13.

FIGS. 13 and 14 show a cross-sectional front view and cross-sectional side view, respectively, of portions of the dies 24, 26, the needle barrel 82 and the suture 84 during the first compression stroke. The upper die 26 is moved slowly downward to press against, and to thereby flatten, the top 86 of the needle barrel 82, compressing the inner surface 94 of the bore 96 against the suture 84. The sides 90, 92 of the needle barrel 82 are restrained from becoming substantially deformed by the curved surface 42 of the groove 40, which prevents the needle barrel 82 from expanding in a lateral direction, (i.e., in a direction substantially perpendicular to the direction of the movement at the upper die 26). Further, the bottom 88 of the needle 82 is restrained by the curved surface 42 so that it is not substantially deformed. During the first compression stroke, the lower surface 30 of the upper die 26 approaches the upper surface 28 of the lower die 22, but does not contact it. The distance $d_s$ by which the lower surface 30 is separated from the upper surface 28 at the end of the downward stroke of the upper die 26 is controlled by the operator of the swaging equipment, and is influenced, in part, by the desired suture pull-out strength and the dimensional tolerances of the dies 24, 26 and the needle barrel 82. Compression of the top 86 of the needle barrel 82 also shapes the needle barrel 82 to conform to the chamfered lower surface of 30 of the upper die 26 to reduce the likelihood of weakening the needle barrel 82 or the suture 84.

Figure 15:
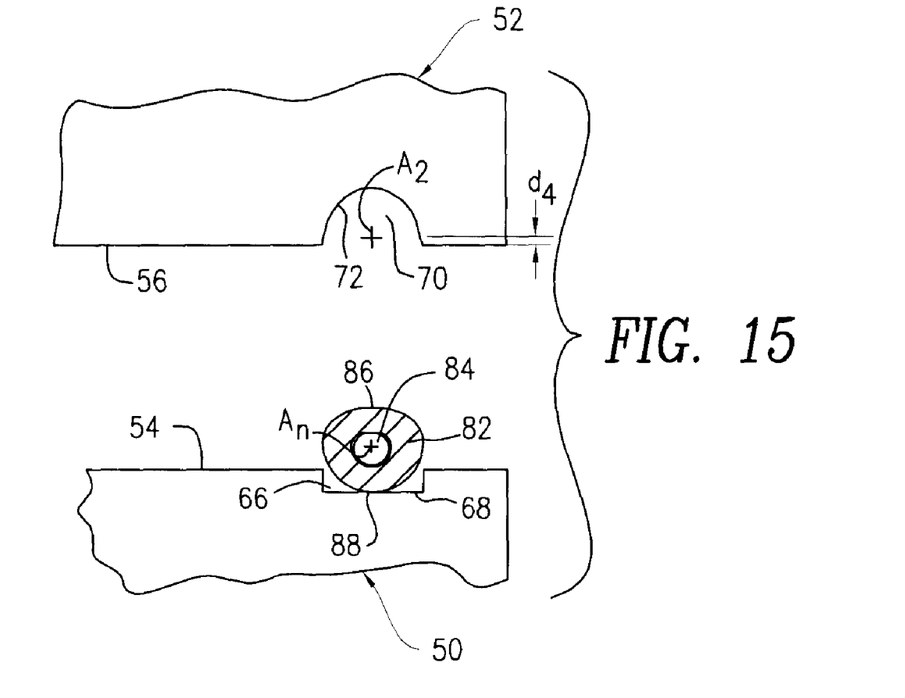
FIG. 15 is a cross-sectional front view of a portion of the swage die set of FIG. 7 with the needle barrel and suture of FIGS. 13 and 14 before the second compression stroke of the two-hit swage process.

FIG. 15 shows a cross-sectional front view of portions of the dies 50, 52 with the aforesaid needle barrel 82 and suture 84 after the first compression stroke, but prior to the second compression stroke. The bottom 88 of the needle barrel 82 rests against the flat surface 68 of the groove 66 in the lower die 50, with the upper die 52 positioned above the flattened top 86 of the needle barrel 82. It can be seen that the longitudinal axis $A_n$ of the needle barrel 82 is above the upper surface 54 of the lower die 50.

Figure 16:
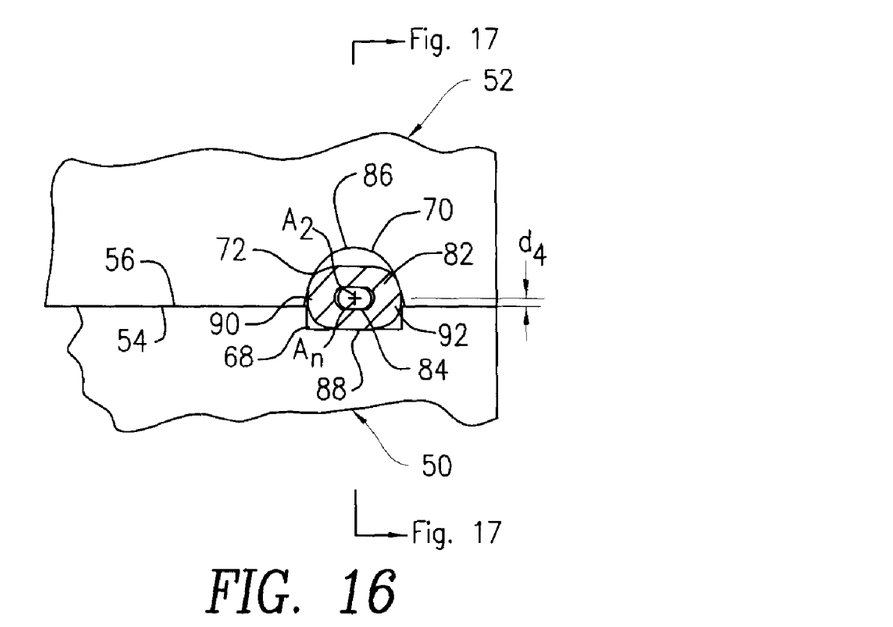
FIG. 16 is a cross-sectional front view of the portion of the swage die set, needle barrel and suture of FIG. 15 during the second compression stroke of the two-hit swage process.
Figure 17:
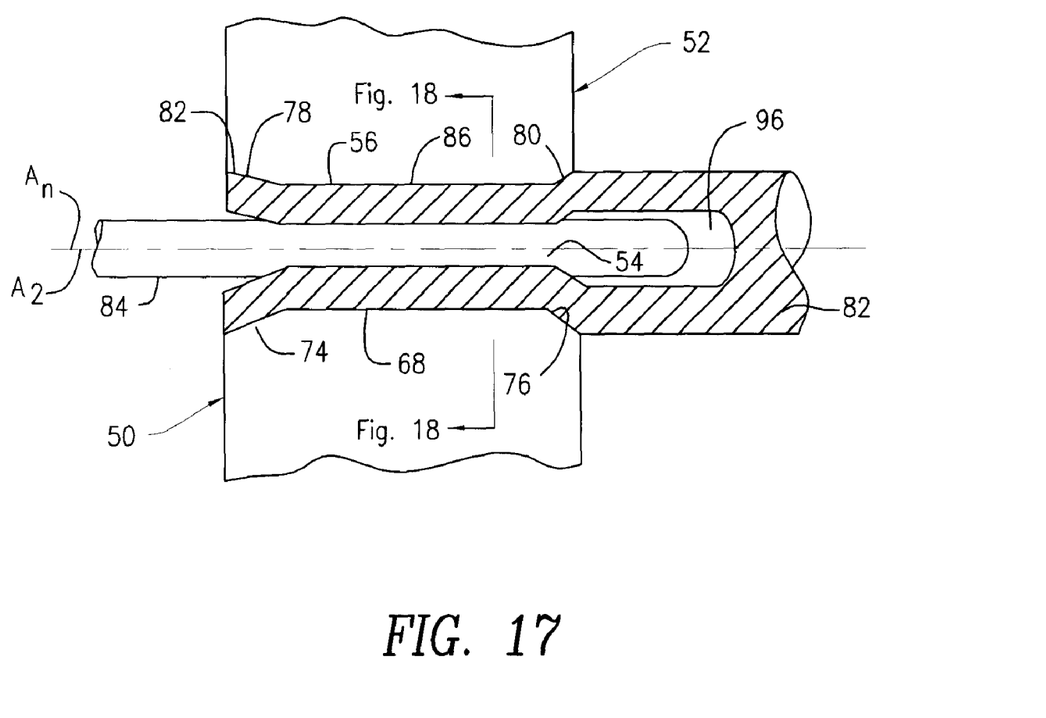
FIG. 17 is a cross-sectional side view of the portion of the swage die set, needle barrel and suture of FIG. 16.

FIGS. 16 and 17 show cross-sectional front and side views, respectively, of portions of the dies 50, 52, the needle barrel 82 and the suture 84 during the second compression stroke. The upper die 52 is moved slowly downward with the curved surface 72 engaging the needle barrel 82 adjacent to its swaged top 86, so as to press the bottom 88 of the needle barrel 82 is against the flat surface 68 of the lower die 50, which further compresses the inner surface 94 of the bore 96 against the suture 84. The sides 90, 92 of the needle barrel 82 are restrained from lateral expansion by contact with the curved surface 72 of the groove 70 in the upper die 52 at about the set-back distance $d_4$. Although the central longitudinal axis $A_n$ of the needle barrel 82 is within the groove 70 at the end of the second compression stroke, the depth of the needle barrel 82 within the groove 70 is limited by contact between the needle barrel 82 and the curved surface 72. The lower surface 56 of the upper die 52 may contact the upper surface 54 of the lower die 50, as illustrated, or the surfaces 54, 56 may remain separated by some distance determined by the operator, based on the desired pull-out force for the suture 84 and the dimensional tolerances of the dies 50, 52 and the needle barrel 82. It may also be observed that the second compression stroke shapes the bottom 88 of the needle barrel 82 to conform it to the shape of the chamfered upper surface 68 of the lower die 54, while the chamfers 78, 80 of the lower surface 56 of the upper die 52 maintain the shape of the compressed top 86 of the needle barrel 82.

Figure 18:
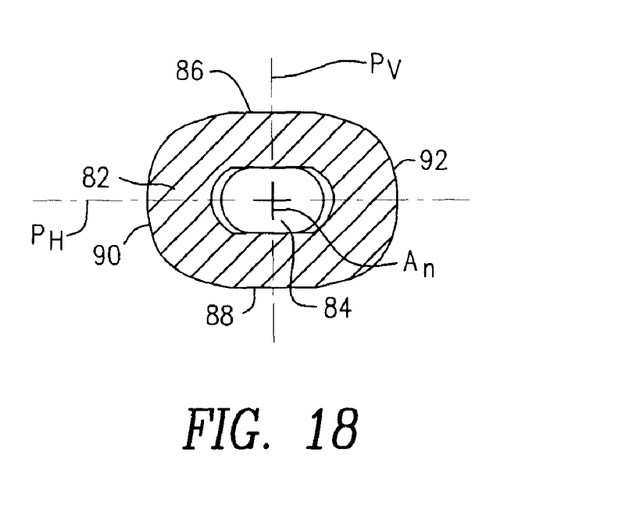
FIG. 18 is a cross-sectional view of the needle barrel and suture of FIG. 17 after the completion of the second compression stroke.

FIG. 18 shows a lateral cross-sectional view of the compressed needle barrel 82 and the suture 84 after the completion of the second compression stroke. The compressed needle barrel 82 is substantially symmetrical about a vertical plane $P_V$ through the central longitudinal axis $A_n$ of the needle barrel 82, having the shape of symmetrical capital "D"s. The compressed needle barrel 82 is also substantially symmetrical about a horizontal plane $P_H$, also through the central longitudinal axis $A_n$. This shape results in reduced stresses at the sides 90, 92, relative to other shapes of compressed needle barrels, reducing the potential for rebound or for cracking of the needle barrel 82, while providing the same or greater pullout forces. Without limiting the scope of the invention, it is believed that putting the flattened side (i.e., the top 86) into the rounded groove 70 during the second compression stroke distributes the stresses accumulated during the first compression stroke away from the lateral "9 o'clock" and "3 o'clock" positions (i.e., sides 90, 92) to other positions, such as "4 o'clock", "7 o'clock", etc, thereby reducing the stresses at the lateral positions.

In an alternate embodiment of the two-hit process, which embodiment is not illustrated in the drawings, both compression strokes are performed at a single work station using a single die set. The die set is similar to the first die set 22 illustrated in FIGS. 3-6, except that the counterpart of the curved surface 42 of the groove 40 in the lower die 24 is chamfered so as to have counterparts to the needle-side and suture-side chamfers 44, 46 present in the upper die 26. In a further alternate embodiment, the second die set 48 illustrated in FIG. 9, may be used with the positions of the upper die 52 and lower die 50 inverted about a horizontal plane. In the aforesaid alternate embodiments of the two-hit process, the first compression stroke is performed in substantially the same manner as was previously described. After the first compression stroke, the needle barrel is removed from the lower die, rotated 180 degrees about its central longitudinal axis, then replaced in the groove of the lower die. The second compression stroke is then performed in substantially the same manner as the first compression stroke.

FIGS. 19-24 relate to a process and apparatus for swaging a needle to a suture in which the needle barrel is compressed against the suture in a single compression stroke (i.e., a "one hit" process). This swaging process is substantially the same as the two-hit process, except as described further herein, and produces a suture-and-needle combination that is essentially the same as that produced by the two-hit process. In a one-hit process, the needle barrel is compressed against the suture in a single compression stroke in which opposite sides of the needle barrel are compressed concurrently by a single set of dies. The die set used in the aforesaid one-hit process, of which an embodiment is described herein, is intended for use with a needle of the same well-known type described in the foregoing discussion of the first and second die sets for use in a two-hit process, and illustrated in FIGS. 1 and 2.

Figure 19:
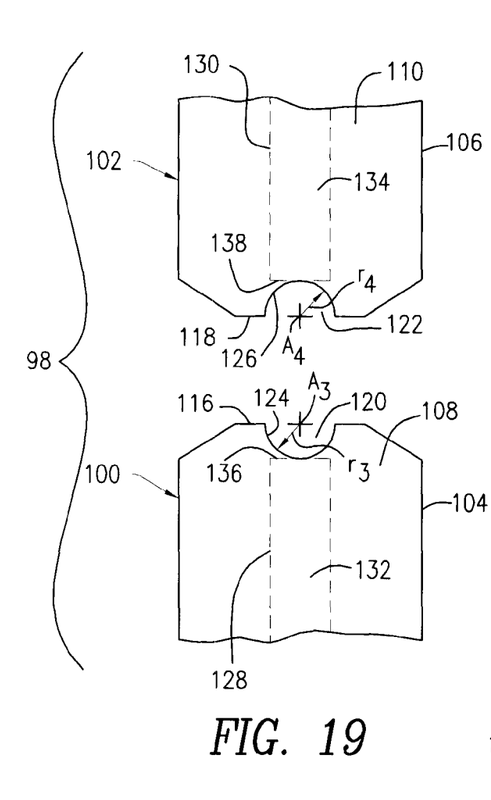
FIG. 19 is a front view of a portion of a swage die set for use in a one-hit swage process according to a second embodiment of the present invention showing interior structures in phantom view.
Figure 20:
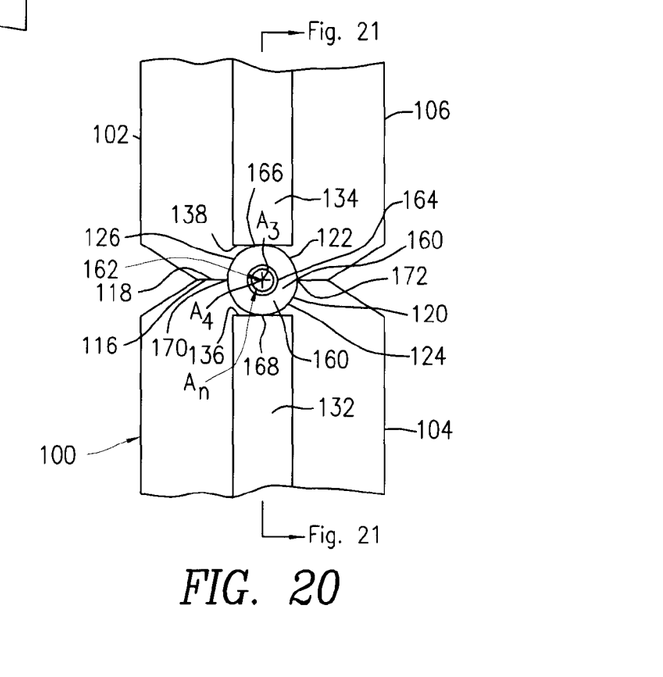
FIG. 20 is a cross-sectional front view of the portion of the swage die set of FIG. 19 with a needle barrel and suture before the compression stroke of the one-hit swage process.
Figure 21:
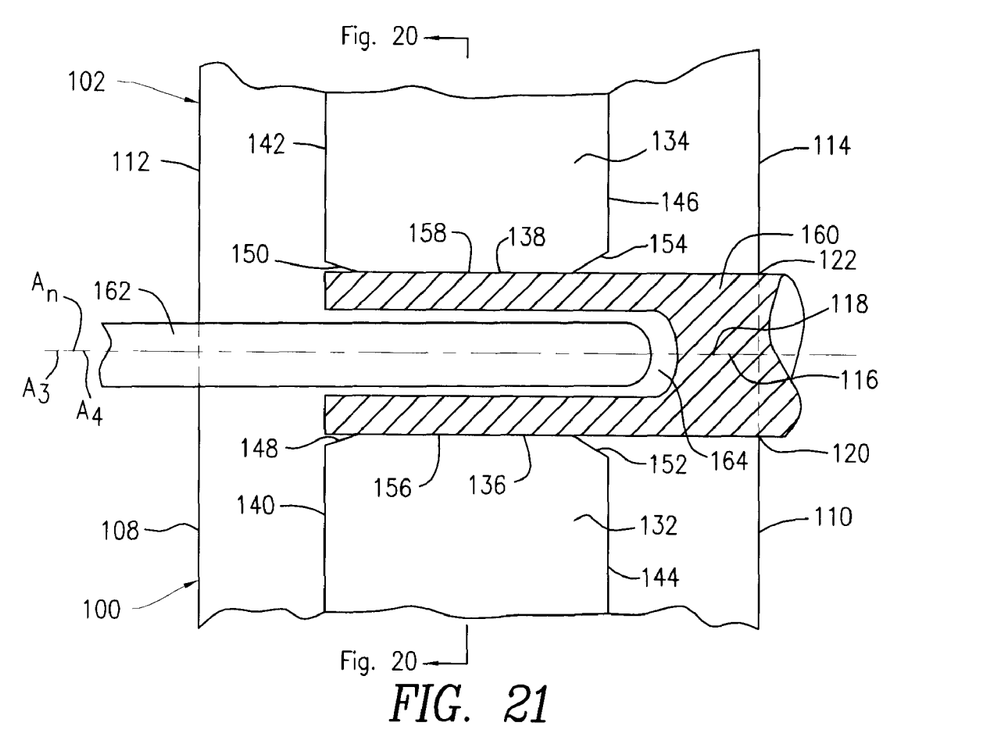
FIG. 21 is a cross-sectional side view of the portion of the swage die set, needle barrel and suture of FIG. 20.

FIGS. 19-23 include schematic views of portions of a die set 98 for use in a one-hit swaging process, with FIGS. 20-23 illustrating the compression stroke of the swaging process. The die set 98 is but one example of numerous die sets and swaging mechanisms that may be used in the one-hit process, and is, similar to the die sets described more fully in U.S. Patent Publication No. 2008/0119876, published May 22, 2008, and corresponding to U.S. patent application Ser. No. 11/601,077, filed Nov. 17, 2006, which publication is incorporated herein by reference in its entirety. Dies 100, 102 have substantially similar structures to each other; however, the one-hit process does not require dies that are identical or mirror images, or that possess the structural features that are shown in FIG. 19-23, but are not discussed herein. The dies 100, 102 are shown oriented in a vertical direction. However, the respective dies 100, 102 could be oriented horizontally or in any other direction, as long as they are substantially opposed to each other and their respective movement is approximately along the same axis, such that they converge and diverge. Terms indicating position, orientation and direction of motion are used throughout the discussion of FIGS. 19-23 in relation to the dies 100, 102 of the die set 98 as illustrated in FIG. 19-21 for the purpose of facilitating discussion, and not to limit the embodiment to the particular ones shown and described.

Referring to the aforesaid FIGS. 19-23, the dies 100, 102 have die bodies 104, 106 with front surfaces 108, 110, back surfaces 112, 114 (see FIG. 21) and end surfaces 116, 118 that are substantially flat, except as otherwise described. End surfaces 116, 118 of the opposed dies 100, 102, respectively, are adapted to come into contact with each other during the swaging process. The die bodies 104, 106 also have grooves 120, 122, respectively, in the end surfaces 116, 118. The grooves 120, 122 are substantially similar to each other, having curved surfaces 124, 126 that are substantially semicircular and having radiuses of curvature $r_3$ and $r_4$ around longitudinal axes $A_3$ and $A_4$, respectively, that are about the same as the radius $r_n$ of a needle barrel 160 that is to be swaged. In one embodiment of the invention, the groove 120 of the lower die 100 may be shaped so that the curved surface 124 has a longitudinal axis $A_3$ that is set back from the end surface 116 of the die 100, in a similar fashion to the groove 40 in the end surface 28 of the lower die 24 shown in FIG. 5.

Continuing to refer to FIGS. 19-23, the dies 100, 102 have rectilinear conduits 128, 130 extending through the respective die bodies 104, 106 and intersecting the respective grooves 120, 122, and narrow stakes 132, 134 that slidably fit within the conduits 128, 130 so that free ends 136, 138 of the stakes 132, 134 can be extended into the grooves 120, 122 and withdrawn into the die bodies 104, 106. Prior to the start of the swaging process, the stakes 132, 134 are in withdrawn positions within the die bodies 104, 106 with the free ends 136, 138 of the stakes 132, 134 inside the die bodies 104, 106. The stakes 132, 134 have respective front surfaces 140, 142 and back surfaces 144, 146, and are positioned so that their respective front and back surfaces 140, 142, 144, 146 have the same orientation as the respective front and back surfaces 108, 110, 112, 114 of the die bodies 104, 106. The orientations of the front surfaces 140, 142 and back surfaces 144, 146 are also referred to herein as the suture sides 140, 142 and needle sides 144, 146, respectively, because, during the swaging process, a suture will extend away from the front surfaces 140, 142 and the portion of the needle that is not compressed will extend away from the back surfaces 144, 146. The free ends 136, 138 of the stakes 132, 134 have chamfers 148, 150 at their respective suture sides 140, 142 and chamfers 152, 154 at their respective needle sides 144, 146. The free ends 136, 138 also have end surfaces 156, 158 between the respective chamfers 148, 150, 152, 154 that are substantially flat and perpendicular to the lengths of the stakes 132, 134. In an embodiment of the invention, the angles of the chamfers 148, 150, 152, 154 relative to the end surfaces 156, 158 are about 15 degrees for the suture-side chamfers 148, 150 and about 30 degrees for the needle-side chamfers 152, 154.

Figure 22:
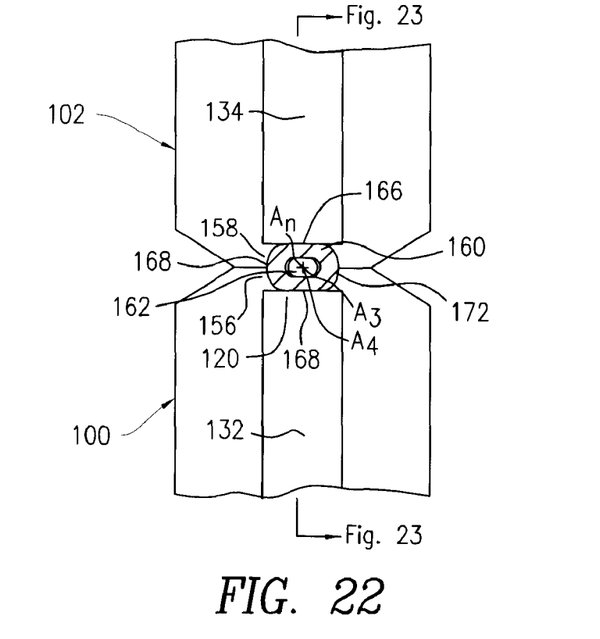
FIG. 22 is a cross-sectional front view of the portion of the swage die set, needle barrel and suture of FIG. 20 during the compression stroke of the one-hit swage process.
Figure 23:
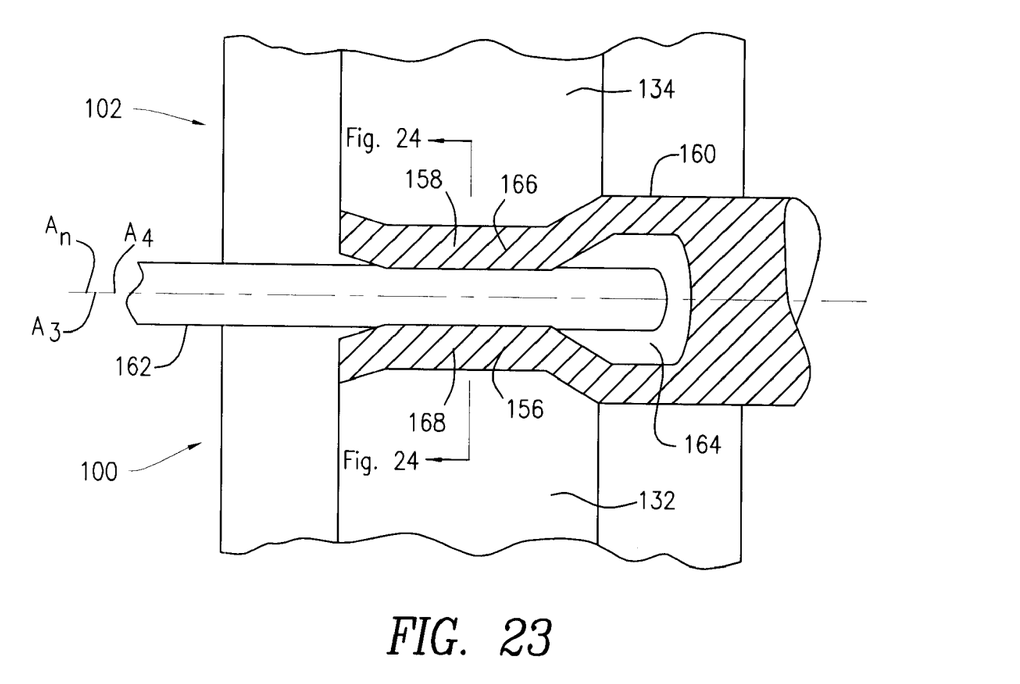
FIG. 23 is a cross-sectional side view of the portion of the swage die set, needle barrel and suture of FIG. 22.

FIGS. 20-23 illustrate the one-hit swaging process, with FIGS. 20 and 21, respectively, being a cross-sectional front view and cross-sectional side view of portions of the die set 98, the needle barrel 160 and the suture 162 prior to the compression stroke. FIGS. 22 and 23, respectively, are a cross-sectional front view and cross-sectional side view of portions of the die set 98, the needle barrel 160 and the suture 162 during the compression stroke. For reference, the needle barrel 160 is shown as having a first radially-defined portion (or "top") 166 at a "12 o'clock" position, a second radially-defined portion 168 (or "bottom") at a "6 o'clock" position and opposed first and second lateral portions (or "sides") 170, 172 at the lateral "9 o'clock" and "3 o'clock" positions, respectively. In FIGS. 20-24, cross-hatching has been removed from all elements, with the exception of needle barrel 160, to improve the clarity of the drawings.

Referring to FIGS. 20 and 21, the dies 100, 102 have been moved from their positions in FIG. 19 toward each other so that their respective end surfaces 116, 118 contact each other. The stakes 132, 134 are aligned and the grooves 120, 122 oppose each other with their respective longitudinal axes $A_3$, $A_4$ generally aligned. A suture 162 has been inserted into the bore 164 of the needle barrel 160. The ends 136, 138 of the stakes are withdrawn into the die bodies 104, 106, with the end surfaces 156, 158 of the stakes 132, 134 adjacent to, or at least closely approaching, the top 166 and bottom 168 of the needle barrel 160, respectively.

The grooves 120, 122 in the die bodies 104, 106 encircle or surround the needle barrel 160. It can be seen that the curved surfaces 124, 126 of the grooves 120, 122 contact the needle barrel 160, or at least closely approach it, such that the sides 170, 172 of the needle barrel 160 will be restrained during the compression stroke. Central longitudinal axis $A_n$ of the needle barrel 160 substantially coincides with the longitudinal axes $A_3$, $A_4$. In an alternate embodiment wherein the longitudinal axis $A_3$ of the curved surface 124 of the groove 120 in the lower die 100 is set back from the end surface 116, the needle barrel 160 would rest in the groove 120 with its central longitudinal axis $A_n$ set back from the end surface 116, similar to the arrangement of the lower die 24 and needle barrel 82 depicted in FIG. 11.

Referring to FIGS. 22 and 23, during the compression stroke, the end surface 158 of the upper stake 134 is pressed against the top 166 of the needle barrel 160, and the end surface 156 of the lower stake 132 is pressed against the bottom 168 of the needle barrel 160. The sides 170, 172 of the needle barrel 160 are restrained from being substantially deformed in the lateral directions (i.e., the "9 o'clock" and "3 o'clock" directions) by the curved surfaces 124, 126 of the grooves 120, 122. The suture 162 is compressed vertically within the bore 164 of the needle barrel 160. The end surfaces 156, 158 of the respective stakes 132, 134 shape the bottom 168 and top 166 of the needle barrel 160 to conform them to the shapes of the chamfers 148, 152 (at the bottom 168) and 150, 154 (at the top 166) to reduce the likelihood of weakening the needle barrel 160 or suture 162.

Figure 24:
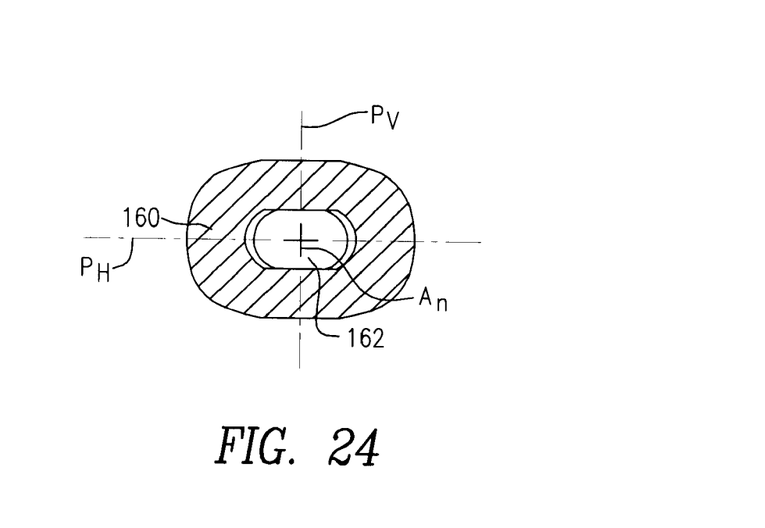
FIG. 24 is a cross-sectional end view of the needle barrel and suture of FIG. 23 after the completion of the compression stroke.

FIG. 24 shows a lateral cross-sectional view of the compressed needle barrel 160 and the suture 162 after the completion of the compression stroke. Similar to the needle barrel 82 depicted in FIG. 18, the needle barrel 160 is substantially symmetrical about a vertical plane $P_V$ and horizontal plane $P_H$ through the central longitudinal axis $A_n$ of the needle barrel 160, and has the characteristic "double-D" shape described with respect to FIG. 18.

It should be understood that the embodiments described herein are merely exemplary and that a person skilled in the art may make many variations and modifications thereto without departing from the spirit and scope of the present invention. All such variations and modifications, including those discussed above, are intended to be included within the scope of the invention, as defined in the appended claims.

What is claimed is:

1. A tool for attaching a suture to a needle barrel having a first radially-defined portion, a second radially-defined portion opposite the first radially-defined portion and first and second lateral portions between the first and second radially-defined portions and opposite each other, and a bore which is formed in an end of the needle barrel and is at least partially defined by opposed inner surfaces, an end of the suture being positioned in the bore, said tool comprising:

a first die set including first and second dies, at least one of said first and second dies being movable relative to the other of said first and second dies, said first die having a first groove therein for receiving the needle barrel such that when said at least one of said first and second dies moves toward said other of said first and second dies, said second die compresses the first radially-defined portion of the needle barrel so as to compress the suture against the opposed inner surfaces of the bore, said first groove being at least partially defined by a curved surface sized and shaped so as to restrain the first and second lateral portions of the needle barrel from moving laterally during the compression of the first radially-defined portion of the needle barrel by said second die; and a second die set including third and fourth dies, at least one of said third and fourth dies being movable relative to the other of said third and fourth dies, said third die having a second groove therein for receiving the needle barrel such that when said at least one of said third and fourth dies moves toward said other of said third and fourth dies, said fourth die compresses the second-radially defined portion of the needle barrel so as to compress the suture against the opposed inner surfaces of the bore, said second groove being at least partially defined by a curved surface sized and shaped so as to restrain the first and second lateral portions of the needle barrel from moving laterally during the compression of the second radially-defined portion of the needle barrel by said fourth die.

2. The tool of claim 1, wherein said needle barrel has a central longitudinal axis, said first groove of said first die being sized and shaped such that the axis of the needle barrel resides within said first groove when the needle barrel is received within said first groove, said second die having a first substantially flat surface at an end thereof, said first groove and said first substantially flat surface being opposable to each other such that, when said at least one of said first and second dies moves toward said other of said first and second dies with the needle barrel received within said first groove such that the axis of the needle barrel is within said first groove, said second die compresses the first radially-defined portion of the needle barrel with said first substantially flat surface, said second groove of said third die being sized and shaped such that the axis of the needle barrel resides within the second groove when said needle barrel is received into said second groove, said fourth die having a third groove in an end thereof with a second substantially flat surface set back into the fourth die, said third groove being arranged to receive the needle barrel with the axis of the needle barrel outside of said third groove, said second groove and said third groove being opposable to each other such that when at said at least one of said third and fourth dies moves toward said other of said third and fourth dies with said needle barrel received within said third groove, said second substantially flat surface presses the needle barrel into said second groove such that the axis of the needle barrel is within said second groove and said second substantially flat surface compresses the second-radially defined portion of the needle barrel.

3. The tool of claim 2, wherein said first groove has a second longitudinal axis therein, said first groove being arranged to receive the needle barrel with the needle barrel resting on said first groove and the second radially-defined portion and the first and second lateral portions of the needle barrel contacting said first groove with the longitudinal axis of the needle barrel generally coinciding said second longitudinal axis, and said second groove has a third longitudinal axis within said second groove, said second groove being arranged to receive the needle barrel such that the first and second lateral portions of the needle barrel contact said second groove when the longitudinal axis of the needle barrel coincides with said third longitudinal axis.

4. The tool of claim 2, wherein each of said first and second flat surfaces has a respective width that is at least twice the radius of the needle barrel in a direction perpendicular to the longitudinal axis of the needle barrel.

5. The tool of claim 2, wherein said first and second grooves are cylindrically-curved grooves.

6. A method of attaching a suture to a needle barrel having a first radially-defined portion, a second radially-defined portion opposite the first radially-defined portion, first and second lateral portions between the first and second radially-defined portions and opposite each other, and a bore which is formed in an end of the needle barrel and is at least partially defined by opposed inner surfaces, an end of the suture being positioned within the bore, said method comprising the steps of:

compressing the first radially-defined portion of the needle barrel with a first substantially flat surface such that the suture is compressed against the opposed inner surfaces of the bore while restraining the first and second lateral portions of the needle barrel from moving laterally during said compressing of the first radially-defined portion; and compressing the second radially-defined portion of the needle barrel with a second substantially flat surface such that the suture is compressed against the opposed inner surfaces of the bore while restraining the first and second lateral portions of the needle barrel from moving laterally during said compressing of the second radially-defined portion.

7. The method of claim 6, wherein said step of compressing the second radially-defined portion of the needle barrel is performed during said step of compressing the first radially-defined portion of the needle barrel.

8. The method of claim 6, wherein said step of compressing the second radially-defined portion of the needle barrel is performed after said step of compressing the first radially-defined portion of the needle barrel.

9. The method of claim 6, wherein the needle barrel has a central longitudinal axis and said first substantially flat surface and said second substantially flat surface are the same substantially flat surface, and said method includes the further step of rotating the needle barrel by 180 degrees about the central longitudinal axis of the needle barrel.

10. The method of claim 6, wherein the needle barrel has a central longitudinal axis and each of said first and second substantially flat surfaces has a respective width that is at least twice the radius of the needle barrel in a direction perpendicular to the central longitudinal axis of the needle barrel.

11. A method of attaching a suture to a needle barrel having a first radially-defined portion, a second radially-defined portion opposite the first radially-defined portion, first and second lateral portions between the first and second radially-defined portions and opposite each other, and a bore which is formed in an end of the needle barrel and is at least partially defined by opposed inner surfaces, an end of the suture being positioned within the bore, said method comprising the steps of:

placing the needle barrel in a restraining device that restrains said first and second lateral portions from moving laterally; and concurrently compressing the first and second radially-defined portions of the needle barrel with a first substantially flat surface of a first tool and a second substantially flat surface of a second tool, respectively, such that the suture is compressed against the opposed inner surfaces of the bore, said restraining device restraining the first and second lateral portions of the needle barrel from moving during said concurrent compressing of the first and second radially-defined portions.

12. In combination, a suture; and a needle including a barrel having a compressed part, which is formed by compressing opposite portions of said barrel with opposed substantially flat surfaces while restraining lateral portions of said barrel that are between said opposite portions from moving laterally during compression, and a non-compressed part adjacent said compressed part, said compressed part having a cross-sectional shape having opposed outwardly curved lateral portions and opposed substantially flat portions between said curved portions, said cross-sectional shape being substantially symmetrical about a first plane that is coplanar with a central longitudinal axis of said barrel and substantially perpendicularly through said flat portions, said compressed part having a width perpendicular to said longitudinal axis that is substantially the same as a width of said non-compressed part perpendicular to said longitudinal axis, said barrel having a bore formed in an end of said barrel and at least partially defined by inner surfaces, said suture having an end positioned within said bore and compressed against said inner surfaces within said compressed section part of said barrel.

13. The method of claim 11, wherein the needle barrel has a central longitudinal axis; and said restraining device includes a first die body having a first end with a first cylindrically-curved groove therein and a second die body having a second end with a second cylindrically-curved groove therein, said first tool being movable within said first die body such that said first substantially flat surface of said first tool enters said first groove and said second tool being movable within said second die body such that said second substantially flat surface of said second tool enters said second groove, said first and second grooves cooperating to form a cylindrical through-hole which receives the needle barrel and restrains the first and second lateral portions thereof from moving laterally with the central longitudinal axis of the needle barrel substantially aligned with a central longitudinal axis of said through-hole, and wherein, during said concurrently compressing step, said first tool moves within said first die body into said first groove and said second tool moves within said second die body into said second groove and said through-hole restrains the first and second lateral portions of said needle barrel from moving laterally.

14. The method of claim 13, wherein each of said first and second grooves has cross-sections in the shape of a half-circle.

15. The combination of claim 12, wherein said cross-sectional shape is substantially symmetrical about a second plane passing through the central longitudinal axis of said barrel and oriented substantially perpendicular to said first plane.

16. The combination of claim 12, wherein said cross-sectional shape is a shape approximating that of two capital "D"s arranged symmetrically about said first plane.

\* \* \* \* \*